United States Patent [19]

Fattore et al.

[11] Patent Number: 4,778,827
[45] Date of Patent: Oct. 18, 1988

[54] CATALYTIC SYSTEM AND PROCESS FOR PRODUCING A MIXTURE OF METHANOL AND HIGHER ALCOHOLS

[75] Inventors: Vittorio Fattore; Bruno Notari, both of S. Donato Milanese; Alberto Paggini, Spino D'Adda; Vincenzo Lagana', Milan, all of Italy

[73] Assignee: Snamprogetti, S.p.A., Milan, Italy

[21] Appl. No.: 918,668

[22] Filed: Oct. 16, 1986

Related U.S. Application Data

[60] Continuation of Ser. No. 694,484, Jan. 24, 1985, abandoned, which is a division of Ser. No. 437,439, Oct. 28, 1982, Pat. No. 4,513,100.

[30] Foreign Application Priority Data

Dec. 2, 1981 [IT] Italy ............................. 25390 A/81

[51] Int. Cl.$^4$ .................. C07C 27/06; C07C 29/15
[52] U.S. Cl. .................................................. 518/713
[58] Field of Search ........................................ 518/713

[56] References Cited

U.S. PATENT DOCUMENTS 3,326,956 6/1967 Davies et al. .
4,122,110 10/1978 Sugier et al. .
4,291,126 9/1981 Sugier et al. .
4,398,050 8/1983 Hofstadt et al. .
4,460,378 7/1984 Di Pietro et al. .
4,481,012 11/1984 Di Pietro et al. .

OTHER PUBLICATIONS

Anderson et al. Industrial & Engineering Chemistry, vol. 44, No. 10 (1952) pp. 2418-2424.

Primary Examiner—Howard T. Mars
Attorney, Agent, or Firm—Hedman, Gibson, Costigan & Hoare

[57] ABSTRACT

A catalytic system and process for producing mixtures of methanol and higher alcohols from synthesis gas, the catalytic system comprising zinc, chromium, copper, one or more alkaline metals, and possibly one or more metals chosen from molybdenum, manganese, lanthanium, cerium, aluminium, titanium and vanadium, either all or only part of said elements being chemically bonded to oxygen and/or together.

7 Claims, No Drawings

CATALYTIC SYSTEM AND PROCESS FOR PRODUCING A MIXTURE OF METHANOL AND HIGHER ALCOHOLS

This application is a continuation of Ser. No. 694,484 filed Jan. 24, 1985, abandoned, which is a divisional application of Ser. No. 437,439, filed Oct. 28, 1982, now U.S. Pat. No. 4,513,100.

This invention relates to a catalytic system and its use in the production of mixtures of methanol and higher alcohols from $H_2$ and CO, with the possible presence of $CO_2$ and inerts.

Said product mixtures are useful in particular as petrol substitutes, and can also be mixed therewith in various percentages for use as fuels for internal combustion engines. Many catalysts are known for the production of methanol in mixture with higher alcohols.

"Catalysis"-Brimet-(Vol. 5) describes among others a catalyst comprising Cu, ZnO and $Cr_2O_3$ in the molar proportions of 82%, 16% and 2% respectively. $K_2O$ must be added to these components to give the necessary selective activity.

A further catalyst described in said source of literature is prepared from $Zn(OH)_2$, $Cu(OH)_2$ and $K_3[Cr(CO_4)_3]\cdot 3H_2O$ in equimolar mixture.

Canadian Pat. No. 273,984 describes a catalyst composed of one or more metal oxides chosen from Ag, Cu, Zn, Mn, Mo, U, and V, and one or more alkaline or alkaline earth oxides, in which the number of atoms of the alkaline metal oxides must be equal to one half the total number of atoms of the other metals.

Finally, in French Pat. No. 2,369,234, the catalyst is composed of Cu, Co, at least one element chosen from Cr, Fe, V and Mn, and at least one alkaline metal, the composition range being fairly wide.

With all these types of catalyst, the productivity and selectivity obtained in producing methanol and higher alcohols are not very high. In addition, said catalysts age rapidly, consequently losing both activity and selectivity. In addition to the said drawbacks, it is known that beyond a certain temperature (300° C.), catalysts which contain copper cannot be used because of methanation. A catalytic system for producing mixtures of methanol and higher alcohols has now been surprisingly discovered, which when placed in contact with CO and $H_2$ and possibly $CO_2$ gives both better productivity and selectivity than normally used catalysts. In addition, it has long stability with time. The use of such a catalytic system according to the invention in place of preceding systems leads to considerably reduced methanation, while the methanol synthesis takes place at a sufficiently high rate, and the hydrogenation of the intermediates leads to more stable products.

The catalytic system according to the present invention is composed of the following elements: zinc, chromium, copper, one or more alkaline metals, of which potassium is preferred, and possibly one or more metals chosen from molybdenum, manganese, lanthanium, cerium, aluminium, titanium and vanadium, either all or only part of said elements being chemically bonded to oxygen and/or together.

All the elements present in the catalytic system can be represented by the following empirical formula:

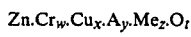

$$Zn\cdot Cr_w\cdot Cu_x\cdot A_y\cdot Me_z\cdot O_t$$

where w lies between 0.1 and 0.8, and preferably between 0.3 and 0.6, x lies between 0.005 and 0.05, and preferably between 0.01 and 0.03, y lies between 0.002 and 0.2, and preferably between 0.01 and 0.1, z lies between 0 and 0.1, and preferably between 0 and 0.04, and t lies between 3.75 and 1.3, its value being that necessary for satisfying the valency with which the various elements appear in the catalyst, A being the alkaline metal or metals, and Me being one or more of the aforesaid possible metals.

The present invention also relates to a process for producing methanol and higher alcohols.

Said process consists of feeding the reaction zone, containing the aforesaid catalyst, with $H_2$, CO and possibly $CO_2$ and inerts in a molar $H_2$:CO ratio of between 0.2 and 10, preferably between 0.5 and 3, at a temperature kept within the range of 330° to 460° C., preferably 360° to 440° C., at a pressure of between 2000 and 30,000 KPa, preferably between 6000 and 18,000 KPa, and at a special velocity of between 5000 and 30,000 GHSV, preferably between 5000 and 15,000 GHSV. The gaseous mixture used for the alcohol formation reaction can be synthesis gas obtained for example from partial combustion of coal, natural gas or hydrocarbons.

The process is carried out by bringing the gaseous mixture into contact with the catalyst in a suitable reactor, which can either be of the fluid or fixed bed type.

The temperature, pressure and spacial velocity should be the most convenient for the catalytic system used, within the range of the aforesaid values.

The catalyst can be prepared by various methods, of which the following are described in particular.

One of these methods comprises adding an alkaline carbonate to an aqueous solution containing salts of zinc, chromium, copper and the element Me in order to obtain a precipitate which is then separated, dried, calcined, fed with the alkaline element, reduced and possibly moulded into the size suitable for the chosen catalytic bed.

The second of these methods comprises reacting zinc oxide with mixtures of ammonium dichromate and alkaline metal dichromates in a ratio such that the final catalyst contains the required quantity of alkaline oxides. The element Me can be added by final impregnation of the already formed catalyst, using a soluble salt such as a nitrate, carbonate, acetate, formate or other organic salt. This is followed by calcining to decompose the salt and to eliminate the anion by evaporation.

Particular care must be taken in reducing the catalyst, which is done either before or after introducing the alkaline metals by diluting the reducing gas, preferably hydrogen or the synthesis gas, with an inert gas such as nitrogen, and controlling the gradually rising temperature in the catalyst bed in such a manner that it does not exceed 350° C. at the end. The catalyst can be prepared either with or without a support. Preferred supports are inert materials of low surface area such as alpha alumina, corundum, mellite, cordierite and silica.

The support can be added either during the catalyst preparation in the precipitation stage or in the final stage by mechanical mixing during pellet formation, extrusion etc. Some non-limiting examples of the invention are given hereinafter for illustrative purposes.

EXAMPLE 1

Catalyst composition in terms of base elements:

$Zn.Cr_{0.35}.Cu_{0.027}.K_{0.02}$ 59 g of chromic anhydride are dissolved in deionised water such as to produce a 30% solution of $CrO_3$ by weight. An aqueous suspension of 140 g of zinc oxide in 2 liters of deionised water is prepared separately.

The chromic solution is added to this suspension, which is kept under strong stirring, and stirring is continued for some hours to ensure complete homogenisation.

The precipitate is filtered off, taken up with water, dried by atomisation and pelletised. The pellets are impregnated with an aqueous ammoniacal solution of copper acetate and potassium prepred as follows.

3.8 g of potassium acetate are dissolved in 3 cc of water. 11 cc of a 32% ammonia solution are added followed by 9.3 g of copper acetate.

The mixture is stirred until completely dissolved, and the already prepared pellets are then impregnated. They are dried at 110° C. in an oven for eight hours, and then calcined at 280° C. for eight hours.

The catalyst is reduced by placing 20 cc of pellets in a copper-clad stainless steel tubular reactor immersed in a bath or fluidised sand, and heated to about 300° C. in a nitrogen stream containing about 2% of hydrogen. During the reduction, the hydrogen flow is controlled so that the temperature does not exceed 350° C. Reduction is complete in about 24 hours.

The catalyst prepared in this manner is ready for the reaction involving synthesis of methanol and higher alcohols.

EXAMPLE 2

Catalyst composition in terms of base elements:

$Zn.Cr_{0.33}.Cu_{0.018}.K_{0.023}$ 1 g of cupric nitrate and 30 g of chromium nitrate are dissolved in 500 cc of deionised water, by heating and stirring vigorously. 18.5 g of zinc oxide are suspended in 500 cc of deionised water. The first solution is poured into the zinc oxide suspension, the mixture then being heated under stirring to 90° C. A quantity of a solution prepared by dissolving 50 g of $K_2CO_3$ in 500 cc of deionised water is then added such as to raise the pH to 9. After one hour the mixture is cooled, neutralised to pH 7 with a 15% solution of nitric acid, and the precipitate is filtered off and washed repeatedly with water. The paste is dried at 110° C. for four hours. The potassium content is determined and found to be 0.8% by weight. Pelletising is then carried out to obtain the catalyst by the procedure described in example 1.

EXAMPLE 3

Catalyst composition in terms of base elements:

$Zn.Cr_{0.33}.Cu_{0.018}Na_{0.06}$

The procedure described in example 2 was followed, but using an $Na_2CO_3$ solution prepared by dissolving 80 g of $Na_2CO_3$ in a liter of water, instead of the $K_2CO_3$ solution. On analysis, the Na content was found to be 1.27%.

EXAMPLE 4

Catalyst composition:

$Zn.Cr_{0.35}.Cu_{0.027}.K_{0.023}.Mn_{0.04}$

The catalyst was prepared by the procedure described in Example 1, but also adding 17.9 g of manganese acetate to the final impregnating solution.

EXAMPLE 5

Catalyst composition:

$Zn.Cr_{0.35}.Cu_{0.027}.K_{0.023}.Al_{0.082}$

The procedure described in example 1 was followed, but also adding 55.72 g of aluminium nitrate to the final impregnating solution.

EXAMPLE 6

Catalyst composition:

$Zn.Cr_{0.4}.Cu_{0.028}.K_{0.023}$

The procedure described in example 1 was followed, but using 66 g of chromic anhydride and 132 g of zinc oxide instead of the quantities stated in example 1.

EXAMPLE 7

Catalyst composition:

$Zn.Cr_{0.45}.Cu_{0.029}.K_{0.02}$

The procedure described in example 1 was followed, but using the following salt quantities:
90 g of chromic anhydride
162 g of zinc oxide
11.7 g of copper acetate
3.4 g of potassium acetate.

EXAMPLE 8 (comparison)

Catalyst composition:

$Zn.Cr_{0.35}.K_{0.02}$

This catalyst was prepared for comparison purposes. The preparation was carried out as described in example 1, but without adding the copper salt to the final impregnation solution.

EXAMPLES 9-15

The catalysts prepared and activated as described in examples 1 to 7 were tested for synthesis of methanol and higher alcohols. A synthesis gas having the following composition was fed:
$H_2$ 66-69%
CO 30-33%
$CO_2$ 0-3%
$CH_4$ 0.1%
$N_2$ 0.3%

The liquid reaction product was separated by cooling and condensation.

Average samples collected after about 24 hours of test operation were analysed by gas chromatography.

The reaction conditions (pressure, temperature, spacial velocity) and the results obtained are given in table 1.

EXAMPLE 16

A life test lasting more than 435 hours was carried out using the catalyst prepared as in example 1.

35 cc of catalyst were placed in a tubular reactor. A synthesis gas mixture of which the composition was kept within the range of values given in example 15 was fed at a throughput of about 10,000 GHSV. The average reaction temperature was 400° C.±5° C., and the operating pressure 13,000 KPa.

The results are given in table 2, and show that there was no substantial variation in productivity or selectivity with time.

EXAMPLE 17 (comparison)

A life test was carried out on the comparison catalyst prepared as in example 8, operating under the same reaction conditions as described in example 16.

The results are given in table 3, and show that this catalyst degenerates with time both in terms of productivity and selectivity, and in addition is much less active from the beginning.

TABLE 1

| Catalyst | Example 9 (Catalyst as in example 1) | | | | | |
|---|---|---|---|---|---|---|
| Pressure KPa | 9,000 | 13,000 | 16,000 | 13,000 | 13,000 | 13,000 |
| Temperature °C. | 398–404 | 397–404 | 397–404 | 398–403 | 398–404 | 416–421 |
| GHSV h$^{-1}$ | 10,650 | 11,400 | 10,340 | 15,030 | 6,870 | 10,650 |
| Methanol % wt. | 57.7 | 61.5 | 68.2 | 66.2 | 54 | 53.2 |
| Ethanol % wt. | 1.9 | 1.6 | 1.3 | 1.4 | 1.8 | 2.3 |
| n-propanol % wt. | 1.5 | 1.7 | 1.4 | 1.6 | 1.8 | 1.8 |
| i-butanol % wt. | 18.1 | 15.8 | 13.6 | 15 | 19.5 | 21.6 |
| Higher alcohols % wt. (C ≧ 5) | 21.5 | 19.3 | 15.5 | 15.5 | 22.5 | 21 |

| | Example | | | | | |
|---|---|---|---|---|---|---|
| Catalyst | 10 (Cat. ex. 2) | 11 (Cat. ex. 3) | 12 (Cat. ex. 4) | 13 (Cat. ex. 5) | 14 (Cat. ex. 6) | 15 (Cat. ex. 7) |
| Pressure KPa | 13,000 | 13,000 | 13,000 | 13,000 | 13,000 | 13,000 |
| Temperature °C. | 392–405 | 398–400 | 397–402 | 399–403 | 398–401 | 396–400 |
| GHSV h$^{-1}$ | 9,560 | 10,200 | 11,170 | 11,400 | 11,800 | 10,200 |
| Methanol % wt. | 71.4 | 78.6 | 67.6 | 79.2 | 69.6 | 57.3 |
| Ethanol % wt. | 1.8 | 1.4 | 2.1 | 1.3 | 1.8 | 1.9 |
| n-propanol % wt. | 1.5 | 1.9 | 3.7 | 1.9 | 2.3 | 2.8 |
| i-butanol % wt. | 9.7 | 8.7 | 14.8 | 8.7 | 14.9 | 16.6 |
| Higher alcohols % wt. (C ≧ 5) | 15.6 | 7.8 | 11.8 | 8.8 | 11.4 | 21.4 |

TABLE 2

| | (Catalyst as in example 1) Hours of operation | | | | |
|---|---|---|---|---|---|
| Catalyst | 47 | 95 | 204 | 326 | 449 |
| Productivity g/hl | 586 | 553 | 586 | 548 | 552 |
| Methanol % wt. | 64 | 67 | 63.6 | 61.5 | 64.6 |
| Ethanol % wt. | 1.7 | 2 | 1.7 | 1.6 | 2.3 |
| n-propanol % wt. | 1.6 | 1.7 | 1.7 | 1.7 | 2.2 |
| i-butanol % wt. | 16.8 | 14 | 16.1 | 15.8 | 16.9 |
| Higher alcohols % wt. (C ≧ 5) | 15.8 | 15.2 | 16.8 | 12.3 | 14 |

TABLE 3

| | (Catalyst as in example 8) Hours of operation | | | | |
|---|---|---|---|---|---|
| Catalyst | 40 | 100 | 245 | 303 | 384 |
| Productivity g/hl | 493 | 485 | 448 | 414 | 357 |
| Methanol % wt. | 80.6 | 82.2 | 83.5 | 84.3 | 85.1 |
| Ethanol % wt. | 2.3 | 2.5 | 2.6 | 2.7 | 2.8 |
| n-propanol % wt. | 4.7 | 5 | 5.2 | 5 | 4.7 |
| i-butanol % wt. | 10.5 | 8.7 | 7.6 | 7 | 6.4 |

TABLE 3-continued

| | (Catalyst as in example 8) Hours of operation | | | | |
|---|---|---|---|---|---|
| Catalyst | 40 | 100 | 245 | 303 | 384 |
| Higher alcohols % wt. (C ≧ 5) | 2 | 1.5 | 1.1 | 0.4 | 1 |

We claim:

1. A process for producing mixtures of methanol and higher alcohols by reacting hydrogen with carbon monoxide at a molar ratio of between 0.2 and 10 in the presence of inerts at a temperature of between 330° and 460° C., a pressure between 2000 kPa and 30,000 kPa and a space velocity between 5000 and 30,000 GHSV in the presence of a catalytic system having the empirical formula:

$$Zn.Cr_w.Cu_x.A_y.Me_z.O_t$$

in which
w lies between 0.1 and 0.8,
x lies between 0.005 and 0.05,
y lies between 0.002 and 0.2,
z lies between 0.0 and 0.1,
t lies between 3.75 and 1.3 its value being that necessary for satisfying the valency with which the various elements appear in the catalyst,
A is at least one alkali metal, and Me is at least one metal selected from the group consisting of molybdenum, manganese, lanthanum, cerium, aluminum, titanium and vanadium.

2. A process according to claim 1, wherein the hydrogen to carbon monoxide ratio is between 0.5 and 3, the temperature is between 360° and 440° C., the pressure is between 6000 and 18,000 kPa and the space velocity is between 5000 and 15,000 GHSV.

3. A process as defined in claim 1 which is carried out in a fluid bed reactor.

4. A process as defined in claim 2 which is carried out in a fixed bed reactor.

5. A process as defined in claim 1 wherein the catalyst is on a support.

6. A process as defined in claim 5 wherein the support is selected from the group consisting of alpha alumina, corundum, mellite, cordierite and silica.

7. A process as defined in claim 1 wherein A is potassium and z is 0.

* * * * *